(12) United States Patent
Ivory

(10) Patent No.: US 9,168,168 B2
(45) Date of Patent: Oct. 27, 2015

(54) PENIS ENHANCING CONDOM

(71) Applicant: Brian Ivory, Boardman, OH (US)

(72) Inventor: Brian Ivory, Boardman, OH (US)

(*) Notice: Subject to any disclaimer, the term of this patent is extended or adjusted under 35 U.S.C. 154(b) by 217 days.

(21) Appl. No.: 13/859,897

(22) Filed: Apr. 10, 2013

(65) Prior Publication Data

US 2013/0269707 A1 Oct. 17, 2013

Related U.S. Application Data

(60) Provisional application No. 61/622,608, filed on Apr. 11, 2012.

(51) Int. Cl.
*A61F 6/04* (2006.01)
*A61F 5/41* (2006.01)

(52) U.S. Cl.
CPC ............. *A61F 6/04* (2013.01); *A61F 2005/411* (2013.01); *A61F 2006/044* (2013.01)

(58) Field of Classification Search
CPC .................... A61F 2005/411; A61F 2006/044; A61F 6/04; A61F 2006/043; A61F 2006/046; A61F 6/005
USPC ........................... 128/842, 844; 604/347–353
See application file for complete search history.

(56) References Cited

U.S. PATENT DOCUMENTS

| 4,919,966 | A  * | 4/1990 | Shlenker ....................... 128/844 |
| 6,983,751 | B2   | 1/2006 | Osterberg |
| 2006/0134611 | A1 * | 6/2006 | Danzy ............................... 435/5 |
| 2012/0181726 | A1 * | 7/2012 | Platt et al. ...................... 264/254 |

* cited by examiner

*Primary Examiner* — Michael Brown
(74) *Attorney, Agent, or Firm* — Robert G. Lev

(57) ABSTRACT

An elongated male condom is constructed with a basic latex sheath, and least partially covered by a sponge-like material for moisture absorption. The sponge-like material is covered by a smooth latex layer having multiple apertures for moisture migration.

11 Claims, 2 Drawing Sheets

PENIS ENHANCING CONDOM

PRIORITY INFORMATION

The present invention relies upon U.S. Provisional Patent Application No: 61/622,608, filed Apr. 11, 2012, for priority.

FIELD OF THE INVENTION

The present invention is directed generally to field of sexual prophylactic devices or male condoms. In particular, the present invention is directed to a penis-enlarging condom configured to enhance or adjust penis size and configuration to better match the anatomy of a sexual partner.

BACKGROUND OF THE INVENTION

There are a wide variety of sexual prophylactic devices (condoms) configured to be applied to the male penis. The most common configuration is a simple latex sheath. In the past, other materials have also been used. All of these have been directed to providing a smooth, impenetrable sheath or casing that would not interfere with tactile interaction of the relevant anatomy. While many existing designs are suitable for prophylactic purposes, they do very little to add to the tactile experience, or to make appropriate adjustments for differences in anatomy with a sexual partner.

Enhancement devices are well-known for conventional condoms. However, they are somewhat limited. These include lubricants, various rib configurations, and even limited penis extensions. However, none of these gradually increase the overall effective size of the penis, without substantial mechanical additions, such as pneumatic inflation. Further, anatomical enhancements when used, are often limited in adjustment and configuration Since compatible size is a very real consideration in sexual intercourse, a device that gradually increases in size while not limiting tactile experience is very much to be desired. However, there is no conventional design that will permit a gradual increase in size and configuration while maintaining protection and an enhanced tactile experience for both partners. The result of a gentle, gradual, fitting of size and configuration between sexual partners would also have therapeutic benefits due to minimal invasiveness. The result would be therapeutic psychological benefits provided by an improved physical sexual arrangement.

SUMMARY OF THE INVENTION

Accordingly, it the primary object of the invention to provide a superior male prophylactic or condom that enhances the sexual experience for both partners, thereby providing therapeutic value.

It is another object of the present invention to provide a condom configured to increase in size without sacrificing the protective utility of the condom.

It is a further object of the present invention to provide a condom capable of effecting desired adjustment between sexual partners, thereby providing therapeutic effect to the act of sexual intercourse.

It is an additional object of the present invention to provide a condom capable of self-adjustment before and during sexual intercourse.

It is still another object of the present invention to provide a condom that facilitates adjustments with regard to the mutual sizes of sexual partners, without the use of a substantial mechanical additions.

It is yet a further object of the present invention to provide a condom that maintains a smooth configuration while maintaining size adjustment and regulation characteristics.

It is again an additional object of the present invention to provide a condom that can be configured for differing sizes along various parts of the length and girth of the condom.

It is still another object of the present invention to provide a condom that permits the selection of certain areas of the condom for greater levels of tactile stimulation.

These and other goals and objects of the present invention are achieved by an elongated condom for the male sexual organ having one open end and an opposite closed end. The condom includes a first contiguous layer of impermeable material and a second layer of sponge-like moisture absorbent material, which extends substantially along the length of the condom. The second layer is covered by a third layer of substantially smooth impermeable material. This third layer has multiple apertures providing access for external moisture to the second layer.

BRIEF DESCRIPTION OF THE DRAWINGS

The drawings described herein after depict only one embodiment, having one configuration of the present invention, which admits to a wide range of embodiments and configurations. Almost any aspect of the present invention as depicted by the subject drawings can be modified to differ substantially from the subject drawings while still remaining within the concept of the present invention.

DETAILED DESCRIPTION OF THE PREFERRED EMBODIMENT

Figure 1:
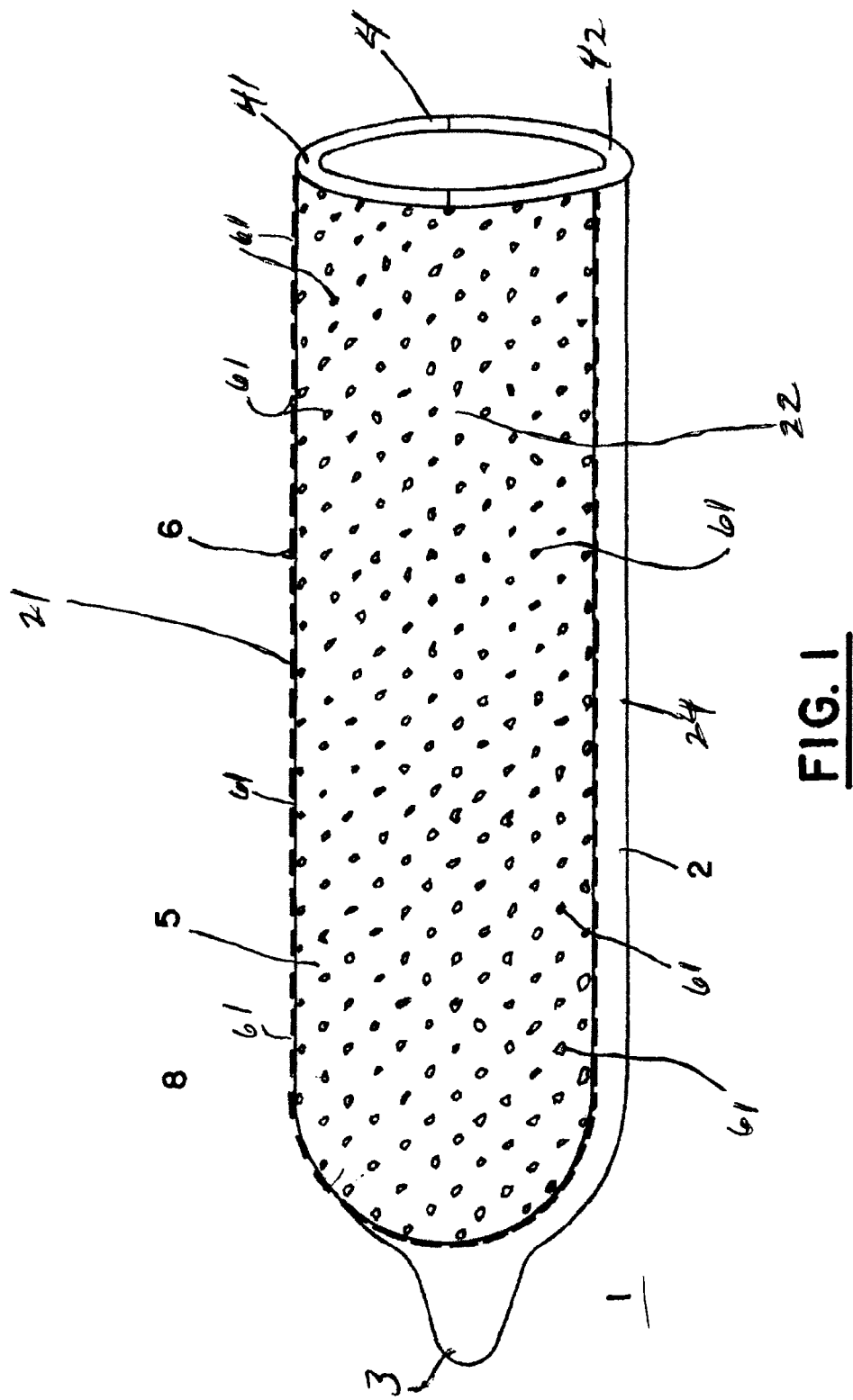
FIG. 1 is a side perspective view of the present invention.

The inventive condom 1 is formed of a sheath 2 made of latex or latex-like material in the same manner as conventional condoms. This includes a closed distal end, preferably in the form of a nipple reservoir 3. The opposite end or proximate end 4 is an opening for the insertion of the male sexual member, as is normal for conventional condoms.

The inventive aspect of the present invention 1 is the self-swelling, or enhancement capability. This comes from layer 5 of thin, compressed, sponge-like material, which absorbs or loses moisture, thereby adjusting girth along the condom length. This sponge-like material is usually cellulose or a cellulose-like material. However, other materials can be used.

As a sponge, layer 5 can absorb varying amounts of moisture such as that generated by female anatomy. Further, other sources of moisture can also be used to adjust the moisture content of the sponge-like layer 5, and thus the size of condom 1. Sponge-like layer 5 can be of varying thicknesses, which can alter at various positions on condom 1. For example, the sponge-like layer 5 can be thicker on sides 22, 23, and thinner on the top 21. Likewise, the bottom 24 can have an extended portion without any sponge at all. This particular embodiment, as depicted in FIGS. 1 and 2, is used to enhance sensitivity for the male sexual organ while providing the benefits of an effectively enlarged male organ due to the sponge-like layer 5 over the rest of the condom.

Figure 2:
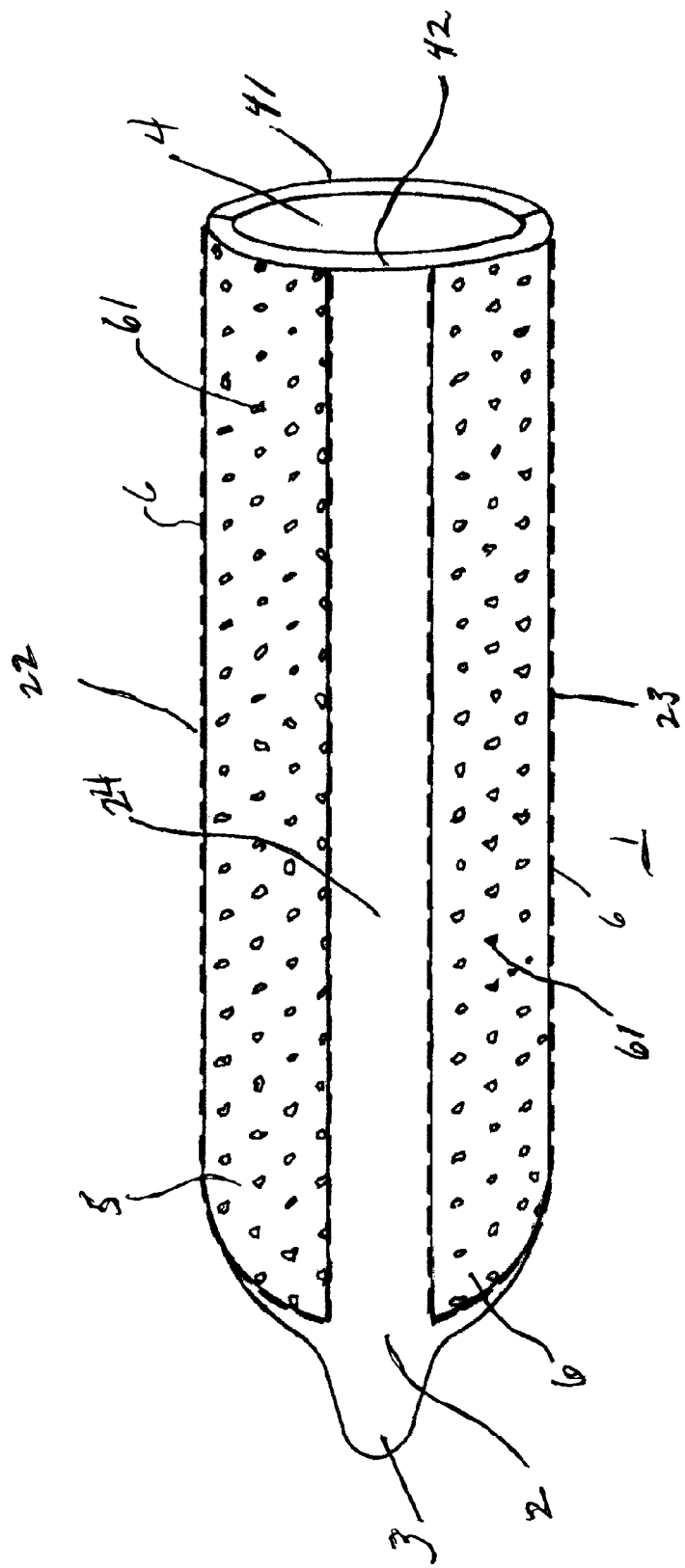
FIG. 2 is a bottom perspective view of the present invention.

It should be understood that condom 1, as depicted in FIGS. 1 and 2, can also be arranged in other shapes. Further, while the sponge-like layer 5 is shown as mostly contiguous over the length and girth of condom 1, this need not be true in all cases. Since the sponge-like material has mostly been removed along the length of the bottom 24 of condom 1, the sponge-like material can be removed in other places. Further, layer 5 need not be uniform at all its locations on the condom 1. Rather, the sponge-like material of layer 5 can be adjusted with varying thicknesses along various parts of the length of condom 1 to better enhance the mutual fit between sexual partners.

The thickness of layer 5 is self-adjusting, based upon its absorption of the surrounding moisture. In this manner, sufficient moisture can be absorbed from the surrounding environment so that condom 1 provides a better fit between sexual partners. If the moisture absorbed increases the size of sponge layer 5 to an inappropriate size, the normal friction and pressure of sexual action will reduce the thickness of sponge-like layer 5 by forcing moisture out of the sponge-like material. The result is psychologically compatibility and a gratifying experience.

The condom 1 can be configured so that there is more sponge, and thus more girth at various parts along the length of condom 1. Further, other parts of condom 1 can be entirely bare of sponge-like layer 5, in order to enhance tactile stimulation at that particular point.

In order to maintain a smooth surface over the entirety of condom 1, the sponge-like layer 5 is covered with a thin latex layer 6. Thus, the overall smoothness of condom 1 is maintained. Layer 6 is covered with apertures 61 to provide access for external moisture to reach the sponge-like layer 5, and for excess moisture to migrate from sponge-like layer 5 through the apertures 61, and away from the surface of the condom 1.

The benefit of the present invention is achieved by the self-swelling capability, whereby moisture from outside of the condom is absorbed through apertures 61 into the sponge-like layer 5. This increases the overall girth of the condom 1, and thus, the effective girth of the male sexual organ employing condom 1. In one example, apertures 61 there are approximately one millimeter in diameter, and approximately one sixteenth of an inch in separation from each other. However, larger apertures 61 can be used, and different spacings of the apertures can be used within the concept of the present invention.

Base 4, constituted by two complimentary annular rings 41, 42 constituting the upper half and lower half, respectively, provides access for the user's sexual organ. Base 4 functions very much in the same manner as any conventional condom. However, the upper and lower halves, 41, 42 can be color coded. This would serve as an aid in properly orienting condom 1 onto the correct portion of the male anatomy so that the positions of the sponge layer 5, or lack thereof (such as on bottom portion 24) can easily be properly positioned. The color coding will aid this positioning, and relieve some of the aggravation often entailed in the application of a male condom.

It should also be understood that while the preferred embodiments of the present invention are configures for the male sexual organ, the same design can be configured for the female sexual organ. In such a configuration (not shown), the arrangement would be substantially reversed with the impermeable portion (latex layer 2) arranged next to the female anatomy. Next, the sponge-like material layer 5 (covered by latex layer 6) will be arranged in manner which most satisfied the requirements of the female anatomy. Further, the sponge-like layer 5 could be arranged to optimize tactile stimulation for both the female and the male anatomies during sexual intercourse.

While a number of embodiments have been provided by way of example, the present invention is not limited thereto. Rather, the present invention should be construed to include any and all variations, modifications, permutations, adaptations, derivations, and embodiments that would occur to one skilled in this technology and having position of the teaching of the present invention. Accordingly, the present invention should be construed as being limited only by the following claims.

I claim:

1. An elongated condom, for a male sexual organ, having an open first end and an opposite closed end to form interior space and an exterior surface, said condom comprising:
   a) a first contiguous layer of a first material impermeable to moisture, forming said exterior surface;
   b) a second layer arranged on an interior surface on said first layer, and comprising a compressed, sponge, moisture absorbent material extending along a substantial length of said elongated condom, said second layer being made of an absorbent material having varying moisture absorbing capacity along the length of said interior space to configure said interior space for enhancing stimulation to a user; and,
   c) a third, substantially smooth layer covering said second layer, said third layer having a plurality of apertures providing access for moisture to pass through from said interior space said third layer and into said second layer, and from said second layer back into said interior space.

2. The elongated condom of claim 1, wherein said condom is shaped for a male sexual organ.

3. The elongated condom of claim 2, wherein said first layer comprises latex.

4. The elongated condom of claim 3, wherein said second layer comprises cellulose.

5. The elongated condom of claim 4, wherein said closed end comprises a nipple reservoir.

6. The elongated condom of claim 5, wherein said first end comprises an annular base.

7. The elongated condom of claim 6, wherein said annular base is color coded for orientation.

8. The elongated condom of claim 4, wherein said condom comprises a bottom portion having a strip free of said cellulose material.

9. The elongated condom of claim 5, wherein said nipple reservoir is free of said sponge material.

10. The elongated condom of claim 4, wherein said second layer is configured to facilitate adaptive swelling over the length and girth of said condom to match a users anatomy and provide enhanced stimulation.

11. The elongated condom of claim 10, wherein said user anatomy is female.

* * * * *